(12) United States Patent
Tuck et al.

(10) Patent No.: US 8,334,416 B2
(45) Date of Patent: Dec. 18, 2012

(54) PROCESS FOR THE PRODUCTION OF 1,2-PROPANEDIOL

(75) Inventors: Michael William Marshall Tuck, London (GB); Robert Wild, London (GB); Simon Nicholas Tilley, London (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 12/747,408

(22) PCT Filed: Dec. 2, 2008

(86) PCT No.: PCT/GB2008/051143
§ 371 (c)(1),
(2), (4) Date: Sep. 10, 2010

(87) PCT Pub. No.: WO2009/074821
PCT Pub. Date: Jun. 18, 2009

(65) Prior Publication Data
US 2011/0004030 A1     Jan. 6, 2011

(30) Foreign Application Priority Data

Dec. 12, 2007   (GB) .................................. 0724232.4

(51) Int. Cl.
*C07C 29/90*     (2006.01)
*C07C 29/88*     (2006.01)
*C07C 29/80*     (2006.01)

(52) U.S. Cl. ........................................ 568/868; 568/861
(58) Field of Classification Search .................. 568/868, 568/861
See application file for complete search history.

(56) References Cited

FOREIGN PATENT DOCUMENTS

| WO | 2007010299 A | 1/2007 |
| WO | 2007053705 A | 5/2007 |
| WO | 2008012244 A | 1/2008 |

OTHER PUBLICATIONS

International Preliminary Report on Patentability for PCT/GB2008/051143, dated Mar. 17, 2010, 12 pages.
International Search Report for PCT/GB2008/051143, dated Mar. 30, 2009, 2 pages.

*Primary Examiner* — Elvis O Price
(74) *Attorney, Agent, or Firm* — Armstrong Teasdale LLP

(57) ABSTRACT

A process for the removal of hydroxypropane from a crude product stream from the hydrogenation of glycerol, the crude product stream comprising 1,2-propanediol and hydroxypropanone as impurity, the process comprising: (a) where required condensing the crude product stream; and (b) contacting the crude product phase in the liquid phase with a stream of a hydrogen-containing gas in the presence of a heterogeneous catalyst at suitable temperatures and pressures such that hydroxypropanone present in the crude product stream is converted to the desired propanediol.

21 Claims, No Drawings

PROCESS FOR THE PRODUCTION OF 1,2-PROPANEDIOL

The present invention relates to a process for the production of 1,2-propanediol or propanols, particularly by the hydrogenation of 1,2,3-propanetriol, also known as glycerol. More particularly it relates to a process for polishing the crude product from the glycerol hydrogenation to remove unreacted hydroxypropanone and other impurities.

Glycerol is available in large quantities and it is anticipated that the supply of glycerol will increase as it is a by-product of processes which are becoming increasingly attractive since they are based on natural products such as oils and fats as starting materials. Examples of oils and fats include palm oil, rape seed oil, beef tallow and the like.

However, whilst glycerol is available in large quantities its present uses are limited in volume. It is therefore desirable to provide processes which enable the glycerol to be converted to useful materials. It will therefore be understood that coupling downstream processes which use glycerol as a feedstock to processes which have glycerol as a by-product offers economic advantages. Thus processes to which a glycerol reactor could be coupled include bio-diesel units and fat splitters such as feed units to natural detergent plants and the like.

Although glycerol does not have uses to match its availability, it can be converted to 1,2-propanediol and propanols which are valuable starting materials which have various applications. Various processes have been proposed for effecting the conversion.

A process is described in U.S. Pat. No. 5,426,249 in which a gaseous stream of glycerol is dehydrated to acrolein. The acrolein is then condensed and hydrated to 3-hydroxypropionaldehyde which is then subjected to hydrogenation in the liquid phase. This multi-step process enables 1,2- and 1,3-propanediol to be obtained simultaneously. An alternative liquid phase process is described in U.S. Pat. No. 5,214,219. Here the glycerol is converted to 1,2-propanediol and 1,2-ethanediol by hydrogenation the liquid phase in the presence of a copper/zinc catalyst and at a temperature of about 220° C.

An alternative processes for the liquid phase hydrogenation of glycerol is described in U.S. Pat. No. 5,616,817. The process, which is directed to the production of 1,2-propanediol, requires the glycerol to have a water content of no more than 20% by weight. The hydrogenation is carried out in the presence of a catalyst comprising cobalt, copper, manganese and molybdenum.

Whilst the processes described above and others offer means for obtaining desirable products from glycerol, they suffer from various disadvantages and drawbacks in terms of conversion, rate and/or economics and it has therefore been suggested that vapour phase hydrogenation should be used. One such process is described in WO 2007/010299, which is incorporated herein by reference, in which a feed comprising glycerol is contacted with a stream of a hydrogen-containing gas and subjected to hydrogenation in the vapour phase in the presence of a catalyst at a temperature of from about 160° C. to about 260° C., a pressure of from about 10 to about 30 bar, a hydrogen to glycerol ratio of from 400:1 to about 600:1 and a residence time of from about 0.01 to about 2.5 secs.

Carrying out the hydrogenation in the vapour phase offers various advantages over the prior art liquid phase processes. In general, the residence time in the hydrogenation reactor is less. This is advantageous since short residence times lead to the formation of fewer by-products than are noted with liquid phase reactions. The described process also makes it possible to operate at lower pressures while maintaining high overall selectivities to the desired products.

An alternative vapour phase for the production of propylene glycol by reaction of a feed material comprising glycerol in the presence of hydrogen is described in WO 2007/057400, which is incorporated herein by reference. This process comprises the steps of:
(a) supplying a stream comprising the feed material to a first vaporisation zone and contacting said feed with cycle gas comprising hydrogen such that at least a portion of the feed is vaporised by and into the cycle gas;
(b) supplying at least a portion of the cycle gas and the vaporised feed material to a first reaction zone comprising catalyst and operating under reaction conditions to allow hydrogenation and dehydration to occur such that a major part of the glycerol is converted;
(c) recovering from the first reaction zone an intermediate product stream comprising cycle gas, minor amounts of unconverted glycerol, and desired product(s);
(d) supplying the intermediate product stream from the preceding reaction zone to a final vaporisation zone and contacting it with additional feed material such that an amount of glycerol, approximately equivalent to that vaporised in the preceding vaporisation zone, is vaporised by and into the intermediate product stream;
(e) supplying the stream from step (d) to a final reaction zone comprising catalyst Other vapour phase processes have been described including those set out in WO 2005/095536 and WO 2007/053705.

Although these vapour phase processes offer various advantages over prior art processes and some lead to the desired product with high yield and selectivity, there are problems associated with separation of the desired product from impurities. Thus whilst vapour phase reactions produce fewer by-products than are noted with the liquid phase reactions, there are still impurities present from which the desired product should be separated, particularly where pharmaceutical grade product is required.

Hydroxypropanone (also known as acetol and hydroxyacetone) is the intermediate in the hydrogenation of glycerol to 1,2-propanediol. Thus after the crude hydrogenation, the 1,2-propanediol rich product stream will contain some "unreacted" hydroxypropanone intermediate. Although hydroxypropanone should be relatively easily separated from the crude product stream by distillation it is still reactive and can form a variety of compounds at the distillation conditions required for the purification process of the 1,2-propanediol. Compounds formed include, but are not limited to, 2,4-dimethyl-2-methanol-1,3-dioxolanes. It will be understood that the dioxolanes and other similar compounds formed are difficult to separate from the 1,2-propanediol by conventional distillation processes since it is these distillation processes which allow these impurities to form. In addition, they have similar boiling points to the desired product. Thus even if there were not the problem of the distillation process causing additional impurities to be formed, it would still not be possible to achieve a satisfactory separation.

It should also be noted that even if it were possible to prevent the formation of the dioxolanes during the distillation procedure the problem would not be overcome since small amounts of the dioxolanes are formed during the vapour phase hydrogenation of the glycerol feed.

It is therefore desirable to provide a process in which the content of hydroxypropanone and its undesirable reaction products in the crude 1,2-propanediol stream produced by the catalytic vapour phase hydrogenation of glycerol is reduced. With this process to will be possible to provide 1,2-propanediol which can be purified particularly to high pharmaceutical grades by conventional distillation processes.

It has been found that passing the crude vapour phase hydrogenation product stream from the vapour phase hydrogenation of glycerol over a liquid phase hydrogenation under suitable reaction conditions in the presence of a heterogeneous catalyst reduces the amount of acetol and its undesirable products to substantially zero therefore allowing very high purity 1,2-propanediol to be obtained using conventional distillation processes. Thus according to the present invention there is provided a process for the removal of hydroxypropanone and 2,4-dimethyl-2-methanol-1,3-dioxolanes from a crude product stream from the hydrogenation of glycerol, the crude product stream comprising 1,2-propanediol and hydroxypropanone and 2,4-dimethyl-2-methanol-1,3-dioxolanes as impurities comprising:

(a) where required, condensing the crude product stream; and (b) contacting the crude product phase in the liquid phase with a stream of a hydrogen-containing gas in the presence of a heterogeneous catalyst at suitable temperatures and pressures such that hydroxypropanone present in the crude product stream is converted to the desired propanediol.

The crude product stream will not generally contain acrolein.

Since the hydroxypropanone is converted to the desired product before being exposed to the distillation conditions, the undesired products which are formed in prior art processes during distillation are not produced. In particular, the dioxolane which can be produced when hydroxypropane is separate from the desired product is avoided. Dioxolane is difficult to separate from the system by distillation.

The process of the present invention will generally provide a purified product stream in which the amount of hydroxypropanone present is reduced to effectively zero. That is to say that its presence and that of its reaction products such as dioxolanes will be typically from about 20 to about 60 ppm when measured by gas chromatography.

The crude product stream which is treated according to the process of the present invention is one which is the product stream from the vapour phase hydrogenation process and which has not been subjected to purification steps. In one arrangement, the product stream from the plant in which the glycerol is reacted in the vapour phase will be passed directly to the process of the present invention. In alternative arrangements, the crude product stream may be stored, either before or after the condensation step, before being subjected to the polishing step of the present invention.

The skilled man will be able to select suitable temperatures and pressures required to achieve the desired result. In general moderate hydrogen pressures and low temperatures will be suitable. A hydrogen pressure of from about 5 to about 45 barg will generally be suitable. Pressures of from about 10 barg to about 25 barg may be preferred. Temperatures in the range of from about 20 to about 200° C. are generally suitable, with those of from about 50 to 130° C. being particularly preferred.

Other conditions can be selected as appropriate. In one arrangement, the liquid product stream is contacted with the hydrogen and passed into a heated hydrogenation zone at a liquid hourly space velocity in the region of about 0.1 to about 10, with liquid hourly space velocities in the range of from about 0.2 to about 5 being particularly preferred.

The hydrogen gas may be supplied at any suitable flow rate with those in the region of about 100 to about 250 h$^{-1}$ GHSV being particularly preferred.

Any suitable catalyst may be used. Examples include nickel, such as in the form of spheres, ruthenium on carbon, ruthenium on nickel, cobalt and copper based catalysts.

The stream from the polishing process of the present invention will have the gas stripped therefrom by conventional means and the product stream can be purified to high purity, such as that of pharmaceutical grade, by conventional distillation methods. The hydrogen gas stripped from the product stream may be recycled.

The stream subjected to the process of the above mentioned first aspect of the present invention may have been formed from glycerol by any suitable process. The process may be in the liquid or the vapour phase. In one arrangement, the process is the hydrogenation of glycerol.

According to a second aspect of the present invention there is provided a process for the hydrogenation of glycerol comprising:

(a) subjecting a feed comprising glycerol to hydrogenation in the presence of a catalyst to form a crude product stream; and (b) subjecting the crude product stream to the process of the above first aspect.

The hydrogenation will preferably occur in the vapour phase.

The process of step (a) may be any suitable arrangement and may be that described in any one of WO 2007/010299, WO 2008/012244, WO 2005/095536 or WO 2007/053705 which are incorporated herein by reference.

In one arrangement, the process of step (a) comprises contacting a feed comprising glycerol with a stream of a hydrogen-containing gas and subjecting the stream to hydrogenation in the vapour phase in the presence of a catalyst at a temperature of from about 160° C. to about 260° C., a pressure of from about 10 to about 30 bar, a hydrogen to glycerol ratio of from 400:1 to about 600:1 and a residence time of from about 0.01 to about 2.5 secs.

In an alternative arrangement, the process of step (a) comprises the steps of:

(i) supplying a stream comprising the feed material to a first vaporisation zone and contacting said feed with cycle gas comprising hydrogen such that at least a portion of the feed is vaporised by and into the cycle gas;

(ii) supplying at least a portion of the cycle gas and the vaporised feed material to a first reaction zone comprising catalyst and operating under reaction conditions to allow hydrogenation and dehydration to occur such that a major part of the glycerol is converted;

(iii) recovering from the first reaction zone an intermediate product stream comprising cycle gas, minor amounts of unconverted glycerol, and desired product(s);

(iv) supplying the intermediate product stream from the preceding reaction zone to a final vaporisation zone and contacting it with additional feed material such that an amount of glycerol, approximately equivalent to that vaporised in the preceding vaporisation zone, is vaporised by and into the intermediate product stream;

(v) supplying the stream from step (iv) to a final reaction zone comprising catalyst.

The present invention will now be described with reference to the following examples. In these test reactions pressures higher than those which would be required on a commercial scale were used.

EXAMPLES 1 to 3

A reactor was charged with catalyst. A crude product stream made in accordance with the process described in WO 2007/010299 was supplied to the reactor and subjected to the process of the present invention. The conditions and results are set out in Table 2.

TABLE 1

| Example No | 1 | 2 | 3 |
|---|---|---|---|
| Feed hydroxypropanone in product from hydrogenation of glycerol wt % | 0.982 | 1.16 | 1.31 |
| Hydroxypropanone after process of present invention wt % | <10-20 ppm | 0.0040 | 0.0038 |
| Reactor Temp ° C. | 110 | 90 | 70 |
| Pressure psig | 600 | 300 | 300 |
| Gas rate nlph | 10 | 12 | 12 |
| Catalyst | Calsicat nickel spheres 86/4 | HTC 500 | HTC 500 + 0.1% Ru |
| LHSV hr$^{-1}$ | 0.5 | 3.5 | 1 |

EXAMPLES 4 and 5

A reactor was charged with catalyst. A crude product stream made in accordance with the process described in WO 2007/010299 was supplied to the reactor and subjected to the process of the present invention. The conditions and results are set out in Table 2.

TABLE 2

| | Example 4 | Example 5 |
|---|---|---|
| Feed hydroxypropanone in product from hydrogenation of glycerol wt % | 1.171 | 1.171 |
| Hydroxypropanone after process of present invention wt % | 0.008 | 0.020 |
| Reactor Temp ° C. | 125 | 125 |
| Pressure psig | 600 | 290 |
| Catalyst | 2 wt % ruthenium on carbon support | 2 wt % ruthenium on carbon support |
| LHSV hr$^{-1}$ | 1.95 | 2.02 |
| Time on Line, h | 132 | 180 |
| Hydroxypropanone Conversion, | 1.171 | 1.171 |

The invention claimed is:

1. A process for the removal of hydroxypropanone and 2,4-dimethyl-2-methanol-1,3-dioxolanes from a crude product stream from the hydrogenation of glycerol, the crude product stream comprising 1,2-propanediol and hydroxypropanone and 2,4-dimethyl-2-methanol-1,3-dioxolanes as impurities, the process comprising:
(a) where required condensing the crude product stream; and
(b) contacting the crude product phase in the liquid phase with a stream of a hydrogen-containing gas in the presence of a heterogeneous catalyst at suitable temperatures and pressures such that hydroxypropanone present in the crude product stream is converted to the desired propanediol and 2,4-dimethyl-2-methanol-1,3-dioxolanes are reduced to from about 20 to about 60 ppm when measured by gas chromatography.

2. A process according to claim 1 wherein the crude product stream is from the vapour phase hydrogenation of glycerol.

3. A process according to claim 1 wherein the pressure of the hydrogen-containing gas is from about 5 to about 45 barg.

4. A process according to claim 1 wherein the temperature at which the condensed crude product is contacted with the hydrogen-containing gas from about 20 to about 200° C.

5. A process according to claim 1 wherein the temperature at which the condensed crude product is contacted with the hydrogen-containing gas from about 50 to 130° C.

6. A process according to claim 1 wherein the liquid product stream is subjected to the hydrogen and passed into a heated hydrogenation zone at a liquid hourly space velocity in the region of about 0.1 to about 10.

7. A process according to claim 1 wherein the liquid product stream is subjected to the hydrogen and passed into a heated hydrogenation zone at a liquid hourly space velocity in the region of about 0.2 to about 5.

8. A process according to claim 1 wherein the hydrogen-containing gas is supplied at a flow rate in the region of about 100 to about 250 h$^{-1}$ GHSV.

9. A process according to claim 1 wherein the catalyst is selected from nickel, nickel spheres, ruthenium on carbon, ruthenium on nickel, cobalt and copper based catalysts.

10. A process for the hydrogenation of glycerol comprising:
(a) subjecting a feed comprising glycerol to hydrogenation in the presence of a catalyst to form a crude product stream; and
(b) subjecting the crude product stream to the process of claim 1.

11. A process according to claim 10 wherein the feed comprising glycerol is subjected to hydrogenation in the vapour phase.

12. A process according to claim 10 wherein the process of step (a) comprises contacting a feed comprising glycerol with a stream of a hydrogen-containing gas and subjecting the stream to hydrogenation in the vapour phase in the presence of a catalyst at a temperature of from about 160° C. to about 260° C., a pressure of from about 10 to about 30 bar, a hydrogen to glycerol ratio of from 400:1 to about 600:1 and a residence time of from about 0.01 to about 2.5 secs.

13. A process according to claim 10 wherein the process of step (a) comprises the steps of:
(i) supplying a stream comprising the feed material to a first vaporisation zone and contacting said feed with cycle gas comprising hydrogen such that at least a portion of the feed is vaporised by and into the cycle gas;
(ii) supplying at least a portion of the cycle gas and the vaporised feed material to a first reaction zone comprising catalyst and operating under reaction conditions to allow hydrogenation and dehydration to occur such that a major part of the glycerol is converted;
(iii) recovering from the first reaction zone an intermediate product stream comprising cycle gas, minor amounts of unconverted glycerol, and desired product(s);
(iv) supplying the intermediate product stream from the preceding reaction zone to a final vaporisation zone and contacting it with additional feed material such that an amount of glycerol, approximately equivalent to that vaporised in the preceding vaporisation zone, is vaporised by and into the intermediate product stream;
(iv) supplying the stream from step (iv) to a final reaction zone comprising catalyst.

14. A process according to claim 10 wherein the crude product stream is from the vapour phase hydrogenation of glycerol.

15. A process according to claim 10 wherein the pressure of the hydrogen-containing gas is from about 5 to about 45 barg.

16. A process according to claim 10 wherein the temperature at which the condensed crude product is contacted with the hydrogen-containing gas from about 20 to about 200° C.

17. A process according to claim 10 wherein the temperature at which the condensed crude product is contacted with the hydrogen-containing gas from about 50 to 130° C.

18. A process according to claim 10 wherein the liquid product stream is subjected to the hydrogen and passed into a heated hydrogenation zone at a liquid hourly space velocity in the region of about 0.1 to about 10.

19. A process according to claim 10 wherein the liquid product stream is subjected to the hydrogen and passed into a heated hydrogenation zone at a liquid hourly space velocity in the region of about 0.2 to about 5.

20. A process according to claim 10 wherein the hydrogen-containing gas is supplied at a flow rate in the region of about 100 to about 250 $h^{-1}$ GHSV.

21. A process according to claim 10 wherein the catalyst is selected from nickel, nickel spheres, ruthenium on carbon, ruthenium on nickel, cobalt and copper based catalysts.

* * * * *